(12) United States Patent
Hommann

(10) Patent No.: US 7,500,966 B2
(45) Date of Patent: Mar. 10, 2009

(54) ADMINISTERING APPARATUS WITH A RESETTABLE ACTIVATING BLOCK

(75) Inventor: Edgar Hommann, Grossaffoltern (CH)

(73) Assignee: TecPharma Licensing AG, Burgdorf (CH)

( * ) Notice: Subject to any disclaimer, the term of this patent is extended or adjusted under 35 U.S.C. 154(b) by 658 days.

(21) Appl. No.: 11/023,297

(22) Filed: Dec. 27, 2004

(65) Prior Publication Data

US 2005/0137571 A1  Jun. 23, 2005

Related U.S. Application Data

(63) Continuation of application No. PCT/CH03/00420, filed on Jun. 25, 2003.

(30) Foreign Application Priority Data

Jun. 28, 2002  (DE)  ................ 102 29 122

(51) Int. Cl.
  *A61M 5/00*  (2006.01)
  *A61M 5/315*  (2006.01)
(52) U.S. Cl. .............. 604/211; 604/187; 604/216; 604/224
(58) Field of Classification Search .......... 604/187, 604/208, 211, 218, 500, 224, 228, 234, 240
See application file for complete search history.

(56) References Cited

U.S. PATENT DOCUMENTS 5,092,842 A  3/1992  Bechtold et al.
6,193,698 B1 *  2/2001  Kirchhofer et al. .......... 604/211

FOREIGN PATENT DOCUMENTS

| DE | 37 15 258 A1 | 11/1988 |
| DE | 41 12 259 A1 | 10/1992 |
| EP | 0 730 876 A2 | 9/1996 |
| EP | 0 897 728 A1 | 2/1999 |
| WO | WO 99/03522 | 1/1999 |
| WO | WO 01/72361 A1 | 10/2001 |

* cited by examiner

*Primary Examiner*—Nicholas D Lucchesi
*Assistant Examiner*—Victoria P Campbell
(74) *Attorney, Agent, or Firm*—David E. Bruhn; Dorsey & Whitney LLP

(57) ABSTRACT

An administering apparatus for administering an injectable substance in doses is provided. The apparatus includes a casing with a reservoir for the substance, a conveying mechanism which acts to deliver a selected dose of the substance from the reservoir, a dosing and activating mechanism which performs a dosing movement and a delivery movement, and which is coupled to the conveying mechanism such that the delivery movement causes the selected dose to be delivered, a dosage indicator sleeve coupled to the dosing and activating mechanism, and a blocking member in a blocking engagement with the dosing and activating mechanism.

15 Claims, 6 Drawing Sheets

ADMINISTERING APPARATUS WITH A RESETTABLE ACTIVATING BLOCK

PRIORITY CLAIM

This application is a continuation of International Patent Application No. PCT/CH2003/000420, filed on Jun. 25, 2003, which claims priority to German Application No. DE 102 29 122 A1, filed on Jun. 28, 2002, the contents of which are incorporated in their entirety by reference herein.

BACKGROUND

The present invention relates to devices and methods for delivering or administering substances and, more particularly, to an administering apparatus for administering an injectable substance or product in selected amounts or doses. The administering apparatus can, in particular, be an injection apparatus, for example an injection pen, such as may be used in many different therapies, for example in diabetes therapy or in administering growth hormone.

Administering apparatus, for example, injection pens, which allow a product or substance dosage to be administered to be selected typically comprise a so-called dosing mechanism which protrudes from a casing opening of the administering apparatus. The dosing mechanism may be button-like, generally similar to the activating button of a ballpoint pen. In order to prepare for the delivery or administration of a substance, the product dosage may be selected by rotating the dosing button relative to the casing. The rotational dosing movement pre-sets a conveying means. For administering, the dosing button is then pressed, from its dosage selection position, a little way into the casing, as far as a front end position. This activates the pre-set conveying means. The conveying means acts on the product or substance contained in a reservoir of the administering apparatus and conveys the selected product dosage, i.e., the product dosage is delivered from the reservoir. In the front end position, the dosing mechanism is blocked against a reverse movement. After the blocking engagement is released, the dosing button is automatically moved back to the dosage selection position and the administering apparatus is ready to administer another dose and, as applicable in some devices, also to select the dosage anew.

Administering apparatus of the type cited above are known, for example, from WO 99/03522 and EP 0 897 728 A1. In the this type of device, however, in order to increase dosing reliability, the reverse movement of the dosing button back to the dosage selection position is only possible if, in the front end position of the dosing button, a dosage indicator of the administering apparatus has been reset to "zero". In these apparatus, the dosage is indicated mechanically with the aid of a dosage indicator sleeve. During the dosing movement of the dosing button, the dosage indicator sleeve is also moved relative to the casing. The position of the dosage indicator sleeve relative to the casing is used to indicate the selected product dosage. In the administering apparatus of EP 0 897 728 A1, two dosage indicator sleeve are required for indicating the selected product dosage, namely, one dosage indicator sleeve for indicating individual dosage units and another dosage indicator sleeve for indicating the dosage units in increments of ten.

In order to reset the dosing button after the product dosage has been administered, the administering apparatus of WO 99/03522 requires two hand operations to be performed: one in order to move the dosage indicator sleeve back to its zero-dosage position and, two, to release a blocking engagement which can only be released in the zero-dosage position of the dosage indicator sleeve. In the administering apparatus of EP 0 897 728 A1, the dosing button is automatically moved back or reset after the two dosage indicator sleeves have been moved back to their zero-dosage position. For the dosing button to be automatically reset by resetting the dosage indicator alone, the dosage indicator sleeve of the two dosage indicator sleeves, which indicate the dosage in increments of ten (the decimal dosage indicator sleeve), is provided with an axial groove. This decimal dosage indicator sleeve surrounds a blocking member which comprises a spring-elastic tongue which is pressed radially inwards by the decimal dosage indicator sleeve into a blocking engagement in which the spring-elastic tongue blocks the resetting movement of the dosing button. If, however, the decimal dosage indicator sleeve is moved to the zero-dosage position, then its axial groove overlaps the spring tongue of the blocking member and the spring tongue can pre-latch radially outwards into the axial groove of the decimal dosage indicator sleeve due to its inherent elasticity force. This pre-latching releases the blocking engagement and the dosing button is automatically moved back to its dosage selection position, driven by the spring force. This resetting mechanism may be susceptible to faults.

SUMMARY

It is an object of the invention to provide a resetting mechanism for resetting a dosing button—or more generally, a dosing and activating means—of an administering apparatus, the resetting mechanism being simple and not susceptible to faults, i.e., accurate and durable or robust.

In one embodiment, the present invention comprises an administering apparatus for administering a substance in selected doses, wherein the apparatus includes a casing with a reservoir for the substance, a conveying mechanism which acts on the substance to deliver a selected dose of the substance from the reservoir, a dosing and activating mechanism which performs a dosing movement for selecting a dose in a dose selection position and a delivery movement in an activating direction as far as a front end position for delivering the selected dose, and which is coupled to the conveying mechanism such that the delivery movement causes the selected dose to be delivered, a dosage indicator sleeve coupled to the dosing and activating mechanism such that the dosage indicator sleeve is moved relative to the casing by the dosing movement of the dosing and activating mechanism to indicate the selected dose, and a blocking member movable into a blocking engagement with the dosing and activating mechanism in the front end position to prevent the dosing and activating mechanism from moving counter to the activating direction, wherein the blocking member can be moved out of the blocking engagement against an elasticity force and wherein a reset cam protrudes from the dosage indicator sleeve, via which the dosage indicator sleeve moves the blocking member out of the blocking engagement when the dosage indicator sleeve is moved to a zero-dosage position relative to the casing.

In one embodiment, the present invention relates to an administering apparatus or device for administering an injectable product in doses comprising a casing with a reservoir for the product, a conveying means, a dosing and activating means, at least one dosage indicator sleeve and at least one blocking member for blocking or locking the dosing and activating means after the product has been delivered.

The conveying means serves to deliver a previously selected product dosage from the reservoir and correspondingly acts on the product situated in the reservoir. In principle, the conveying means can be formed by any type of pump. In some preferred embodiments, however, a piston arranged in the reservoir and a piston rod form the conveying means. The piston and the piston rod can be moved in an advancing direction to deliver the selected product dosage through the outlet of the reservoir by advancing the piston towards the outlet. The piston and the piston rod can be fixedly connected to each other, but in some preferred embodiments the piston rod contacts or presses loosely against the rear side of the piston and, during the dosage selection procedure, exhibits a slight distance from the piston.

In some embodiments, the dosing and activating means comprises a dosing and activating button and a transfer means which is coupled to the dosing and activating button on the input side with respect to selecting the dosage and activating, and on the output side forms the coupling with the conveying means. The dosing and activating button and the transfer means can be formed in one piece. Forming them in multiple pieces is preferred in some embodiments, wherein the multiple pieces may be connected rigidly to each other with respect to the dosing movement.

In some embodiments, the product dosage to be administered is selected using the dosing and activating means and delivered by activating the dosing and activating button. Correspondingly, the dosing and activating means can perform a dosing movement relative to the casing for selecting the product dosage in a dosage selection position, and can perform a delivery movement from the dosage selection position in an activating direction as far as a front end position, for delivering the selected product dosage. In some embodiments, the activating direction is the same as the advancing direction of the piston rod, though this is not required. The dosing and activating means is coupled to the conveying means such that delivery movement of the dosing and activating means causes the selected product dosage to be delivered by the conveying means. In one preferred embodiment of the conveying means, in which a displacing piston and a piston rod completely or partially form the conveying means, the dosing and activating means is coupled to the piston rod, for example by threaded engagement, directly or via a transfer element. Selecting a dosage is no longer possible in the front end position, either because the dosing and activating means is no longer accessible for the user in a suitable way for selecting the dosage, because it is decoupled from the conveying means in the front end position, or because it is no longer accessible and is decoupled.

In some embodiments, the dosage indicator sleeve is coupled to the dosing and activating means such that it is moved relative to the casing by the dosing movement of the dosing and activating means to indicate the selected product dosage. In some embodiments, a pointer indicates the selected product dosage on a dosage scale. In some embodiments, the dosage indicator sleeve is provided with the dosage scale, while the pointer is formed by the casing. In principle, however, the reverse arrangement is also conceivable.

In some embodiments, in order to block the dosing and activating means the blocking member is in a blocking engagement with the dosing and activating means in the latter's front end position, to prevent a resetting movement of the dosing and activating means, i.e., a movement by the dosing and activating means from the front end position counter to the activating direction. In some embodiments, the blocking engagement is configured such that the resetting movement can only be performed when the dosage indicator sleeve assumes the zero-dosage position, i.e., when it assumes, of its positions relative to the casing, the position corresponding to a zero-dosage. In some preferred embodiments, the blocking engagement is formed between the blocking member and the dosing and activating button directly. However, the blocking engagement can also be formed between the blocking member and the transfer means which couples the dosing and activating button to the conveying means.

In accordance with the present invention, in some embodiments, the blocking member can be moved out of the blocking engagement against an elasticity force, which conversely means that the elasticity force causes the blocking member to move into the blocking engagement. A cam protrudes from the dosage indicator sleeve, via which the dosage indicator sleeve presses the blocking member out of the blocking engagement when the dosage indicator sleeve is moved to the zero-dosage position. Since the blocking engagement is released by the cam of the dosage indicator sleeve, thus enabling the dosing and activating means to be automatically reset, this cam may be referred to in the following as a reset cam.

Releasing the blocking engagement by means of the reset cam is advantageous with regard to the inevitable production tolerances in the manufacture of the parts of administering apparatus, since the demands on the precision of positioning and forming the reset cam are significantly lower than for a groove into which the blocking member is to pre-latch, as in the administering apparatus of EP 0 897 728 A1. The present invention has the additional advantage that in the zero-dosage position of the dosage indicator sleeve, the positive lock provided by the reset cam prevents the blocking member from persisting in the blocking engagement. The device and method of the present invention is, therefore, not reliant on elasticity forces for releasing.

In some embodiments, the reset cam extends only far enough in the direction or directions in which the dosage indicator sleeve can be moved so that the blocking member is definitely free from the reset cam when the dosage indicator sleeve assumes the nearest settable dosage position to the zero-dosage position, relative to the casing. In some embodiments, the dosage indicator sleeve is preferably secured against moving from larger dosage positions beyond the zero-dosage position.

In some embodiments, the dosage indicator sleeve and the blocking member preferably surround each other, i.e., at least one of said two parts is sleeve-shaped or comprises a sleeve portion. In one preferred embodiment, the dosage indicator sleeve surrounds the blocking member. In this embodiment, the reset cam preferably protrudes from an inner surface area of the dosage indicator sleeve towards the blocking member.

In some embodiments, the reset cam may be continuously widened on at least one side via which it leads onto the blocking member when the dosage indicator sleeve moves to the zero-dosage position, as far as the surface area of the dosage indicator sleeve from which it protrudes, in order that the blocking member and the reset cam slide off of each other in the manner of oblique planes during this movement. In one preferred embodiment, in which the movement of the dosage indicator sleeve is or comprises a rotational movement, the reset cam is widened in the circumferential direction towards the surface area. If the movement of the dosage indicator sleeve is a superimposed movement consisting of a rotational movement and a translational movement, the reset cam can advantageously also be widened towards its foot region in the translational direction towards the side via which it leads onto the blocking member in the direction of the translational movement.

In a preferred embodiment, the blocking member forms a counter reset cam, against which the reset cam presses in the zero-dosage position of the dosage indicator sleeve, in order to release the blocking engagement. The counter reset cam may also be tapered towards its free end facing the reset cam, on the side via first comes into contact with the reset cam when the dosage indicator sleeve moves to the zero-dosage position, i.e., the counter reset cam may also be gradually widened towards its foot region.

As already mentioned, the dosage indicator sleeve can form the dosage scale or the pointer of the dosage indicator; in some preferred embodiments, it forms the dosage scale. The dosage scale can be formed on an upper surface area of the dosage indicator sleeve such that it runs back into itself. When selecting the dosage in such an embodiment, however, the dosage indicator sleeve may only be able to perform a single revolution, as a result of which the indicator fineness would suffer, or the dosage which could be selected would be very limited. A solution comprising multiple dosage indicator sleeves would be conceivable, but would increase the complexity of the mechanism. In order to avoid these disadvantages, in some embodiments, the dosage scale can encircle a longitudinal axis of the dosage indicator sleeve in a spiral. Essentially the same advantage would also be achieved if a dosage scale encircling in a spiral on the casing were provided and the dosage indicator sleeve formed the pointer for said dosage scale. Using a dosage scale encircling in a spiral, it is possible to select a large dosage with sufficient dosing fineness and good legibility of the dosage scale. If the dosage scale is spiral, the movement of the dosage indicator sleeve should correspondingly be a movement composed of rotation and translation. In one preferred embodiment, the dosage indicator sleeve is coupled to the casing via a threaded engagement, in order to obtain such a superimposed, well-defined movement.

In accordance with a preferred embodiment of the present invention, the dosing and activating button is either spring-elastic, or supported spring-elastically on the transfer means, in the activating direction. The same elasticity force against which the dosing and activating button spring-deflects in the activating direction pushes counter to the activating direction, against a stopper. The spring deflection is advantageous for the delivery movement, since the user of the administering apparatus cannot simply press against a fixed stopper when activating the dosing and activating means. Rather, in the front end position of the dosing and activating means, the dosing and activating button spring-elastically gives a little way further in the activating direction under the pressure from the user. In order to spring-deflect the dosing and activating button relative to the transfer means in this way, the blocking member preferably forms a stopper in the blocking engagement. If the blocking member is inserted into a cavity formed on the dosing and activating button in order to establish the blocking engagement, such a cavity can exhibit a greater extension in the activating direction than would be possible with a rigid stopper of the dosing and activating button, due to the spring-deflection movement.

As already mentioned, in some embodiments, the blocking member is moved into a cavity formed on the dosing and activating means, preferably on the dosing and activating button, in order to establish the blocking engagement. In one preferred embodiment, a groove which encircles on an upper surface area of the dosing and activating means forms the cavity. Equally, however, the cavity in its entirety can also be formed by a plurality of separate cavities which are formed on such an upper surface area spaced from each other, in some preferred embodiments, circumferentially. In principle, a single cavity at a single point on the dosing and activating means would alone be sufficient, but would be disadvantageous with respect to selecting the dosage.

BRIEF DESCRIPTION OF THE DRAWINGS

FIGS. 10a-d, depicts an embodiments of the dosage indicator sleeve in accordance with the present invention, in multiple representations.

DETAILED DESCRIPTION

Figure 1:
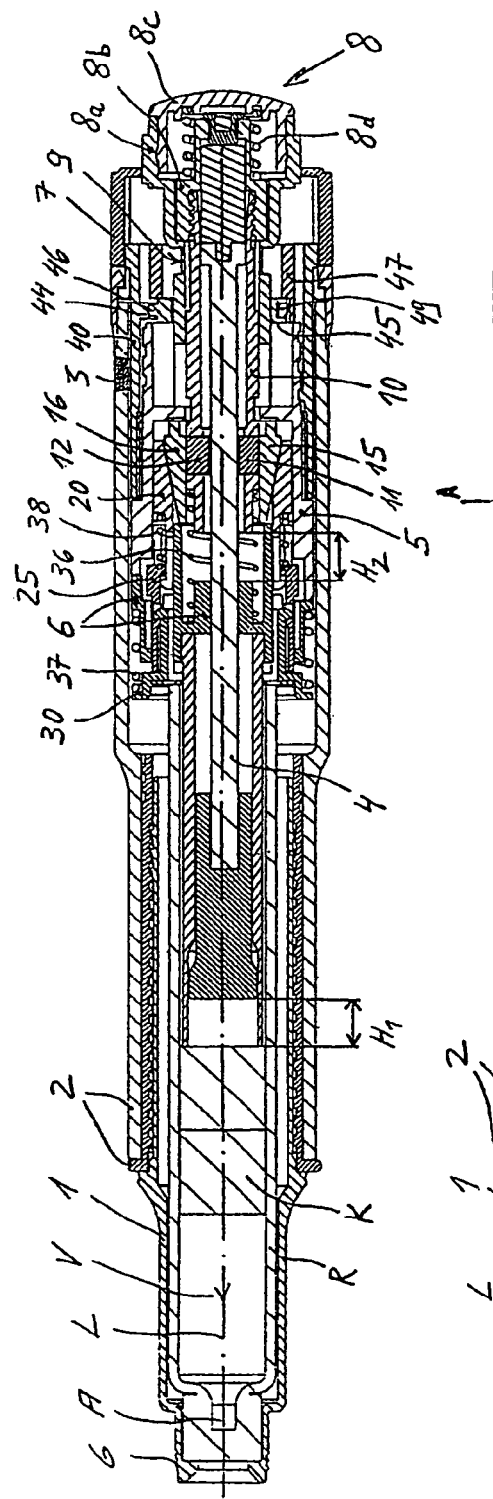
FIG. 1 depicts a product delivery device in accordance with the present invention in an initial state, before a dosage is selected for the first time.
Figure 2:
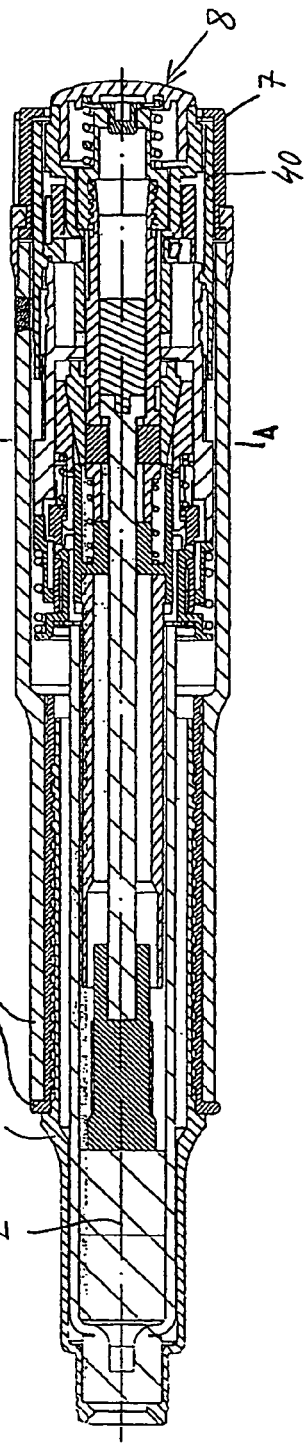
FIG. 2 depicts the product delivery device of FIG. 1 in an end state, in which a piston rod of the device assumes a foremost position and is in engagement with a dosing member.
Figure 3:
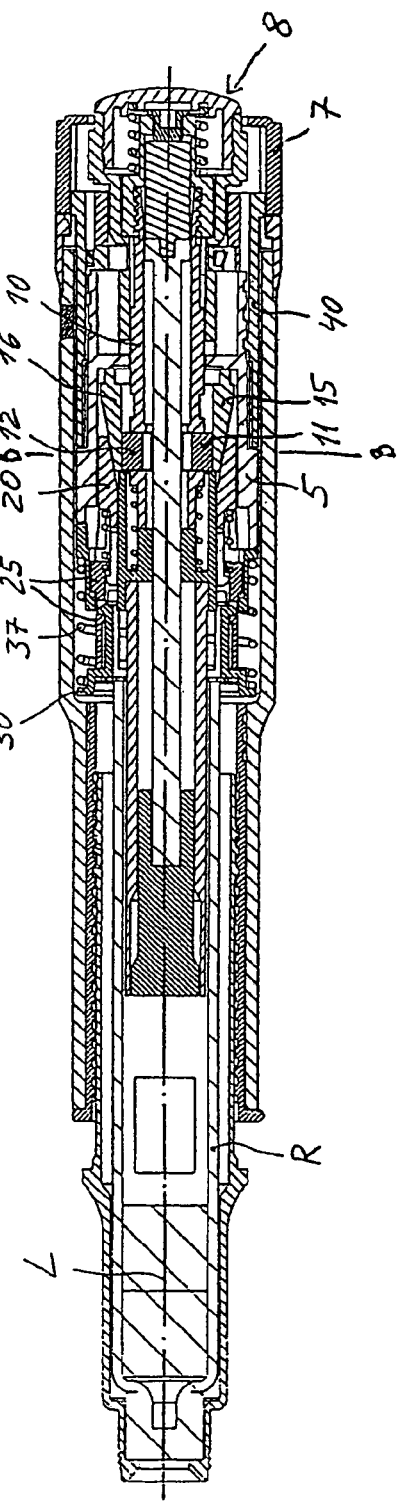
FIG. 3 depicts the product delivery device of FIG. 1 in a state in which the piston rod and the dosing member are out of engagement and the piston rod has been reset to a rearmost initial position.

The figures, including FIGS. 1-3, show one embodiment of a device for delivering a selected dosage of a liquid product or substance. The product can in particular be a medicine or a therapeutic substance, for example insulin.

In one embodiment, the device comprises a casing in two parts, comprising a first, front casing portion 1 and a second, rear casing portion 2, which are each formed as sleeve parts. The two casing portions 1, 2 are screwed together. The front casing portion 1 contains a reservoir R filled with the product. The reservoir R is formed by an exchangeable container, in the example embodiment by a hollow-cylindrical ampoule. The container is inserted from the rear into the front casing portion 1 until it abuts a stopper formed by the front casing portion 1. At its front end, the container comprises an outlet A which is sterily sealed by a septum. In order to be able to deliver the product from the reservoir R formed in this way, a cannula is introduced through the septum into the outlet A. At its rear end, the reservoir R is sealed tight by a piston K. Product is displaced from the reservoir R, i.e. delivered through the outlet A, by advancing the piston K in an advancing direction V, towards the outlet A, along a longitudinal axis L.

The piston K is moved in the advancing direction V by means of a piston rod 4 which is linearly guided along the longitudinal axis L, i.e. axially, by the casing. The piston rod 4 is operably coupled to a dosing and activating means which, in one embodiment, comprises a dosing sleeve 7, a sleeve-shaped dosing and activating button 8 and a sleeve-shaped transfer element 10. A split dosing member comprising, in one embodiment, two separate identical parts or members 11, 12, is connected to said dosing and activating means. The dosing member is split axially into the two parts 11, 12. The two parts are referred to in the following as the first dosing member 11 and the second dosing member 12. The first dosing member 11 and the second dosing member 12 are each in a threaded engagement about the longitudinal axis L, which is simultaneously also the longitudinal axis of the piston rod 4, with the piston rod 4 which is formed as a threaded rod. The first dosing member 11 and the second dosing member 12 are connected, secured against shifting axially and secured against rotating with respect to rotations about the longitudinal axis L, to the transfer element 10. However, both the first dosing member 11 and the second dosing member 12 can be moved relative to the transfer element 10 and in particular relative to the piston rod 4 in a transverse direction with respect to the longitudinal axis L. In order for them to be able to move in the transverse direction, the transfer element 10 linearly guides the first dosing member 11 and the second dosing member 12 by forming a guiding shaft pointing generally transversely with respect to the longitudinal axis L for each of the two dosing members 11, 12, the guiding shaft simultaneously also acting as a block against axial shifting and a block against rotating. As, for example, can be perceived on the basis of FIGS. 6 and 7, each of the guiding shafts comprises a side wall 10a pointing in the advancing direction V and a side wall 10b pointing counter to the advancing direction V. The side walls 10a, 10b each form a linear transverse guiding rail, pointing transversely with respect to the longitudinal axis, for one of the dosing members 11, 12. Each one of the dosing members 11, 12 is enclosed and slide-guided between the two transverse guiding rails 10a, 10b of a guiding shaft, such that the two transverse guides formed by the pairs of transverse guiding rails 10a, 10b only permit sliding movements exactly perpendicular to the longitudinal axis L. The dosing members 11, 12 themselves form the guided engagement sliding pieces. The transverse guiding rails 10a, 10b, in conjunction with the dosing members 11, 12, form a part of a cam gear.

Figure 8:
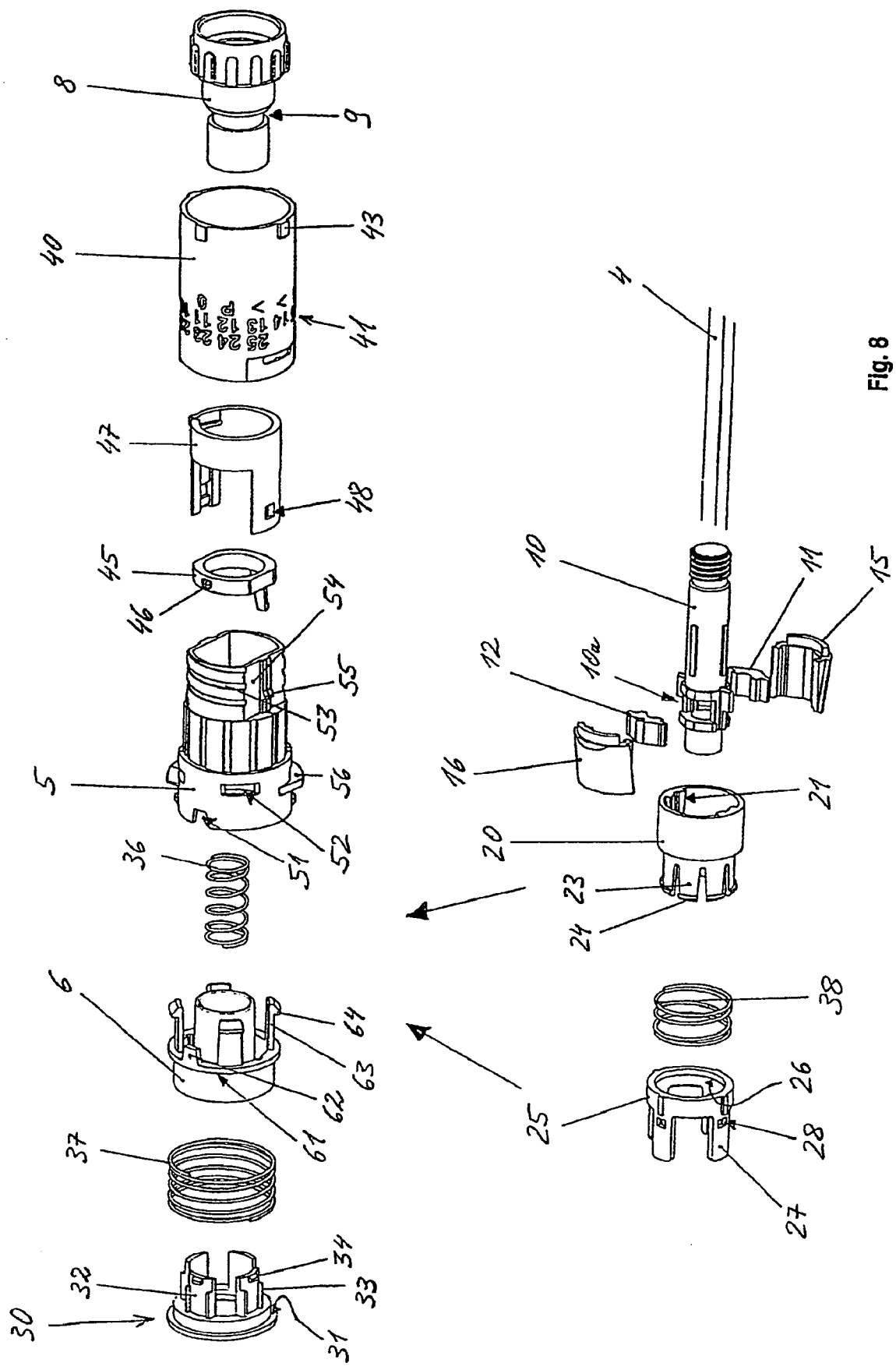
FIG. 8 depicts components of an embodiment of the device in accordance with the present invention in a three-dimensional representation.

With respect to the form, function and co-operation of the components which co-operate for dosing and delivering the product, reference should additionally be made to FIG. 8.

In one embodiment, the dosing and activating button 8 is detachably connected to the transfer element 10. The dosing and activating button 8 is composed of multiple individual parts, namely an outer sleeve part 8a protruding out of the rear casing portion 2, an inserted inner sleeve part 8b, an end button 8c which is inserted from the rear into the outer sleeve part 8a and locked, and a spring 8d which is axially tensed between the end button 8c and the inner sleeve part 8b. The inner sleeve part 8b serves to fasten the dosing and activating button 8 to the transfer element 10 and may, therefore, be referred to in the following as the fastening part 8b. The outer sleeve part 8a is accessible for the user for activating the administering apparatus and may, therefore, be referred to in the following as the activating part 8a. The activating part 8a is connected, secured against shifting, to the end button 8c and supported on the fastening part 8b via the pressure-tensed spring 8d. The activating part 8a can be moved in and counter to the advancing direction V relative to the fastening part 8b and therefore also relative to the transfer element 10. The spring 8d presses the activating part 8a counter to the advancing direction V until it abuts the fastening part 8b, such that it assumes the rear stopper position, shown in FIGS. 1 to 3, relative to the fastening part 8b. Correspondingly, it can be moved relative to the fastening part 8b and the transfer element 10 in the advancing direction V by pressing against the elasticity force of the spring 8d. This ability to move in the advancing direction V is advantageous for activating the dosing and activating means, which, due to this feature, can spring-deflect into itself.

In the following, the components 8a to 8d may be referred to in their entirety as the dosing and activating button 8.

An encircling groove 9 is formed on the outer surface area of the dosing and activating button 8, in the exemplary embodiment on the outer surface area of the outer sleeve part 8a, in a portion surrounding the transfer element 10. The groove 9 co-operates with a blocking member 45 which is formed annularly, surrounds the outer surface area of the dosing and activating button 8, and is tensed radially inwardly against the outer surface area of the dosing and activating button 8 by means of a spring element 49.

Figure 9:
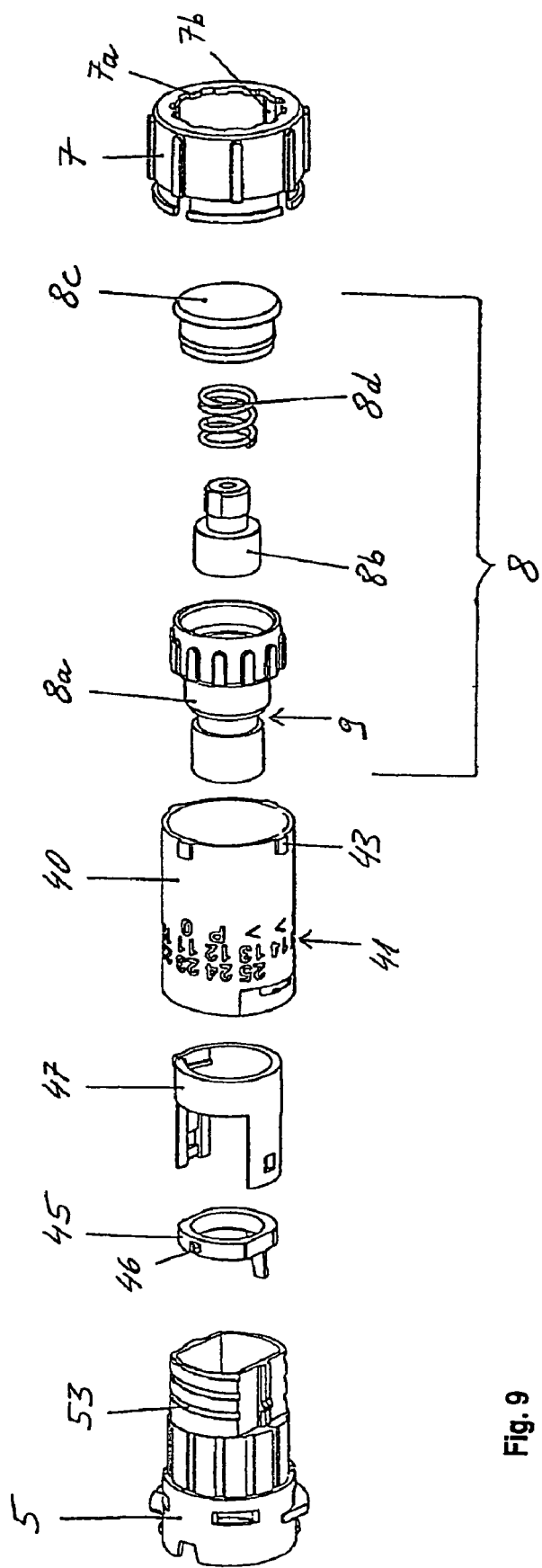
FIG. 9 depicts a dosage indicator sleeve and components in accordance with the present invention co-operating with the dosage indicator sleeve in a three-dimensional representation.

The dosing sleeve 7 is attached to the rear end of the rear casing portion 2 and can be rotated about the longitudinal axis L, relative to the rear casing portion 2. At its rear end, the dosing sleeve 7 forms a collar which protrudes radially inwardly and forms teeth 7a (FIG. 9) uniformly distributed over its inner circumference. On an outer surface area opposite the teeth 7a, the dosing and activating button 8 forms linear, axial guiding grooves at a corresponding pitch, in each of which one of the teeth 7a is axially and linearly guided. In this way, the dosing sleeve 7 and the dosing and activating button 8 are secured against rotating about the longitudinal axis L, but are connected such that they can move axially relative to each other.

A piston rod holder 6 forms an axial linear guide for the piston rod 4. The piston rod holder 6 is connected to the rear casing portion 2 such that it cannot move, in particular the piston rod holder 6 can neither be axially moved relative to the rear casing portion 2 or rotated about the longitudinal axis L. The piston rod holder 6 and the piston rod 4 can only move axially relative to each other. In this way, the piston rod 4 is axially and linearly guided relative to the rear casing portion 2.

Between a rear end of the piston rod holder 6 and a collar, protruding radially inward, of a mechanism holder 5, a sliding piece 15 is radially mounted over the first dosing member 11 and another sliding piece 16 is radially mounted over the second dosing member 12, each secured against shifting axially, but radially and linearly guided and, in this sense, able to move radially. The sliding pieces 15, 16 have the same form and fulfil the same function, each with respect to the assigned first dosing member 11 and second dosing member 12. The sliding pieces 15, 16 are arranged symmetrically with respect to the longitudinal axis L. The mechanism holder 5 is connected immovably to the rear casing portion 2, so it cannot move axially relative to the rear casing portion 2, to which end the three-quarter rib 56 serves as a stopper, and cannot rotate about the longitudinal axis L.

The sliding pieces 15, 16 form additional gear members of the cam gear. Since they are each in direct engagement with one of the dosing members 11, 12, they may be referred to in the following as the gear output members of the cam gear. They each co-operate with a gear input member 20 formed as a sliding sleeve and referred to in the following using this designation. The sliding sleeve 20 forms another cam member and the two sliding pieces 15, 16 each form an engagement member of the cam gear. The sliding sleeve 20 can be axially moved relative to the first dosing member 11 and second dosing member 12, the two sliding pieces 15, 16, and relative to the rear casing portion 2. Furthermore, it can be rotated about the longitudinal axis L relative to the rear casing portion 2. A circular cylindrical inner surface area of the mechanism holder 5 forms a rotational sliding bearing and an axial linear guide for the sliding sleeve 20.

Figure 4:
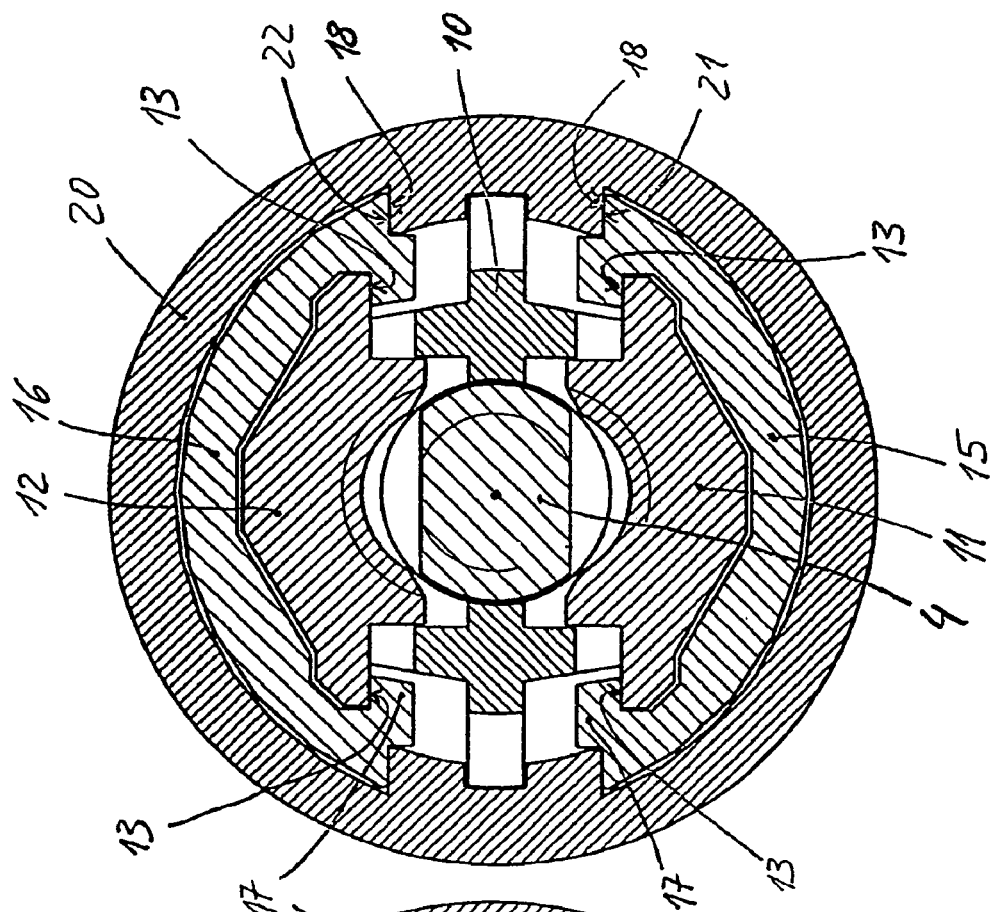
FIG. 4 is a cross-section along line A-A in FIG. 2.
Figure 5:
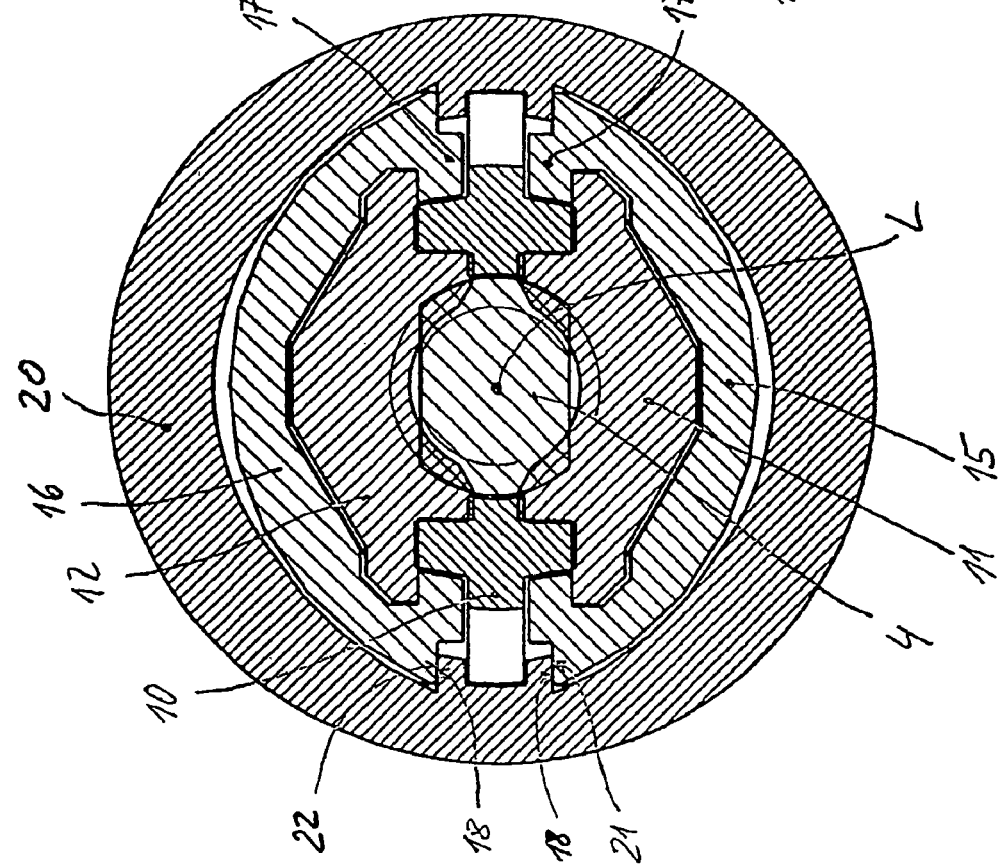
FIG. 5 is a cross-section along line B-B in FIG. 3.
Figure 6:
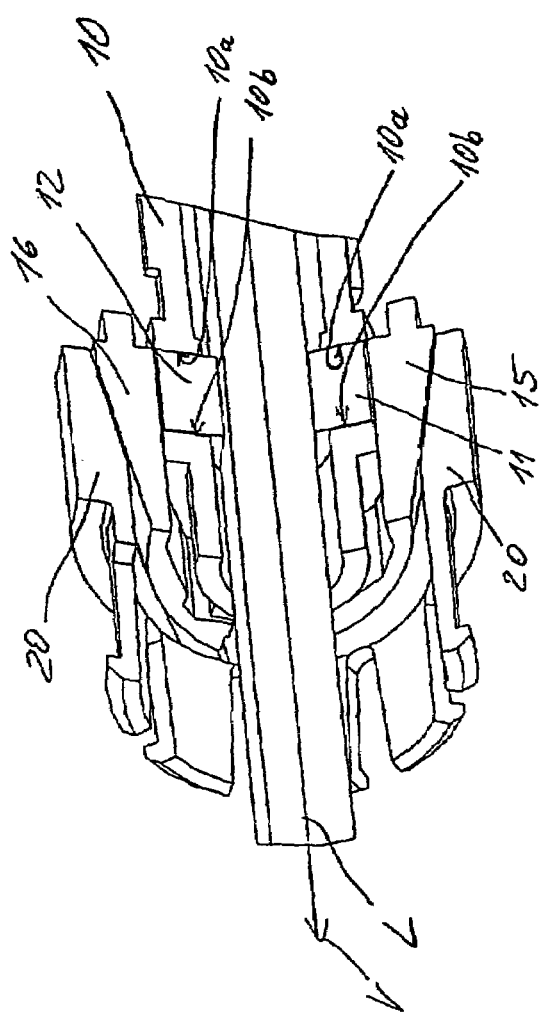
FIG. 6 depicts the piston rod, the dosing member and gear members of a cam gear in a three-dimensional section, wherein the piston rod and the dosing member are in engagement.
Figure 7:
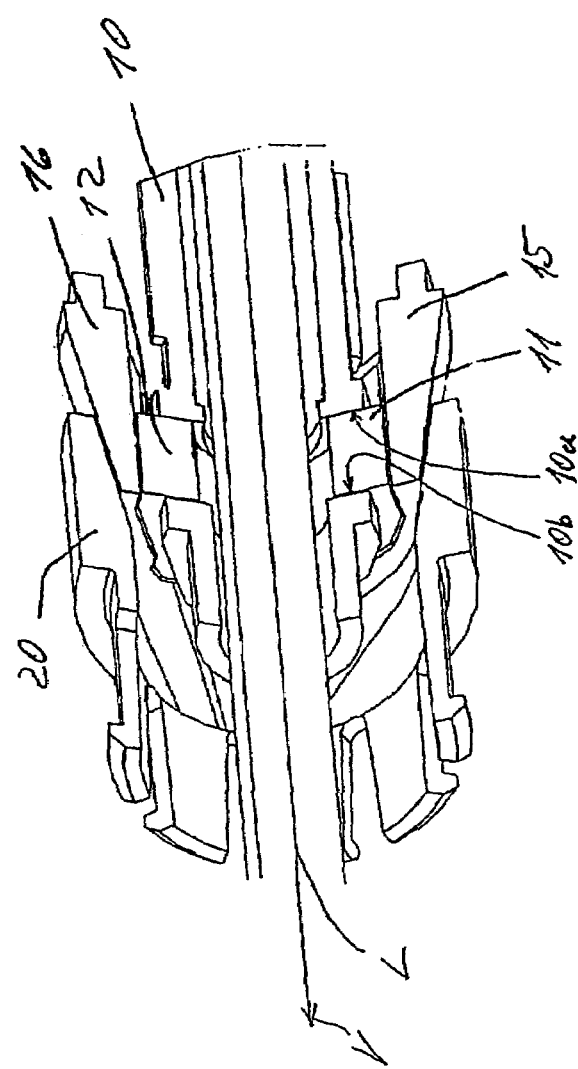
FIG. 7 depicts the piston rod, the dosing member and the gear members in a three-dimensional section, wherein the piston rod and the dosing member are out of engagement.

FIGS. 4 and 5 show the cam gear with the split dosing member and the piston rod 4, each in the same cross-section, relative to the dosing member, but in different gear states. The same gear states are shown in FIGS. 6 and 7, each in a three-dimensional section. Regarding the mode of operation of the cam gear, reference should additionally also be made to FIGS. 4 to 7.

The sliding pieces 15, 16 are each conical on their outer surface. The sliding sleeve 20 forms a corresponding counter cone on its inner surface facing the conical areas of the sliding pieces 15, 16. The conical outer areas of the sliding pieces 15, 16 and the area of the counter cone of the sliding sleeve 20 are generally parallel to each other, forming a conical gap which is uniformly wide over the entire conical areas.

As can be perceived in FIGS. 4 and 5, the sliding sleeve 20 forms two guiding rails 21 for the sliding piece 15 and two guiding rails 22 for the sliding piece 16. The sliding pieces 15, 16 form corresponding engagement rails 18 which are in sliding contact with the guiding rails 21, 22. The guiding rails 21 are formed on the inner surface area of the sliding sleeve 20, diametrically opposed to each other on both sides of the longitudinal axis L. The same applies to the guiding rails 22. The guiding rails 21, 22 extend in the axial direction and each exhibit a substantially constant inclination with respect to the longitudinal axis L, i.e., the guiding rails 21, 22 are linear. The guiding rails 21 are generally parallel to each other, as are the guiding rails 22. The guiding rails 21, 22, formed on the left-hand side and right-hand side of the sliding sleeve 20 in the cross-section in FIGS. 4 and 5, run sagittally towards each other in the advancing direction V—as seen in the longitudinal section in FIG. 1—at an acute angle bisected by a straight line parallel to the longitudinal axis L. When the sliding sleeve 20 moves axially relative to the sliding pieces 15 and 16, the sliding pieces 15 and 16 are thus guided via their engagement rails 18 on the guiding rails 21, 22, such that the sliding pieces 15, 16 are moved away from each other or towards each other transversely with respect to the longitudinal axis L, in this exemplary embodiment, exactly perpendicularly with respect to the longitudinal axis L.

The first dosing member 11 is accommodated, axially and linearly guided, in the sliding piece 15. The second dosing member 12 is correspondingly accommodated, axially and linearly guided, in its sliding piece 16. On their mutually facing lower sides, on the left-hand and right-hand side in the cross-section, the sliding pieces 15, 16 comprise stays 17 which protrude or extend inwardly towards each other. The sliding piece 15 grips behind the first dosing member 11 with its two stays 17, and the sliding piece 16 grips behind the second dosing member 12 with its two stays 17. If the two sliding pieces 15, 16 are moved away from each other, generally transversely with respect to the longitudinal axis L, then the stays 17 gripping behind the dosing members 11 and 12 move the two dosing members 11, 12 away from each other, generally transversely with respect to the longitudinal axis L, in the same way, and thus move them out of engagement with the piston rod 4. When the sliding pieces 15, 16 move transversely towards each other, the sliding pieces 15, 16 again also press the dosing members 11, 12 towards each other via their surface areas, and thus back into engagement with the piston rod 4. As already mentioned, the dosing members 11, 12 are axially guided in their respective sliding piece 15 and 16 such that they can shift linearly. The stays 17 form guiding rails for the linear guide, and the dosing members 11, 12 form engagement rails 13 guided on them, which the stays 17 grip behind.

The threaded engagement between the piston rod 4 and the split dosing member which exists in the state in FIG. 1 is released by the casing portions 1, 2 moving axially relative to each other. This relative movement occurs when the casing portions 1, 2 are screwed apart. When the casing portions 1, 2 are screwed apart, the casing formed jointly by the casing portions 1, 2 is initially lengthened, which corresponds to the casing portions 1, 2 moving axially relative to each other. The relative movement between the casing portions 1, 2, for example for exchanging the reservoir R, is thus used to release the engagement between the piston rod 4 and the split dosing member and the block against the piston rod 4 and the dosing and activating means axial shifting obtained by this engagement.

In order to be able to use the casing portions 1, 2 moving axially relative to each other to release the engagement, the sliding sleeve 20 is connected to the front casing portion 1 in such a way that it is slaved in its axial movement relative to the rear casing portion, while the sliding pieces 15, 16 retain their axial position relative to the rear casing portion 2. Mounting the sliding pieces 15 and 16 between the mechanism holder 5 and the piston rod holder 6 ensures, as mentioned, that the sliding pieces 15, 16 are secured against shifting axially. The coupling of the sliding sleeve 20 on the front casing portion 1 forms a reservoir holding spring 37 which is axially pressure-tensed between the piston rod holder 6 and a reservoir holder 30 when the two casing portions 1, 2 are completely screwed together. To this end, the reservoir holding spring 37 is tensed between the piston rod holder 6 and the reservoir holder 30. The reservoir holding spring 37 presses the reservoir holder 30 against the rear edge of the container which forms the reservoir R. The reservoir holding spring 37 presses the container against a stopper area formed in the front casing portion 1. Arranging such a reservoir holding spring 37 is common in order to equalise length tolerances of the container, the casing portions 1, 2 and the components on which the container is supported in the longitudinal direction.

A slaving means 25 is fastened, secured against shifting and secured against rotating, to the reservoir holder 30. The slaving means 25 forms a transfer member between the reservoir holder 30 and the sliding sleeve 20, when the reservoir holder 30 follows an axial movement of the front casing portion 1 due to the spring force of the reservoir holding spring 37. The sliding sleeve 20 and the slaving means 25 grip behind each other such that the sliding sleeve 20 is slaved by the slaving means 25 during the axial movement. In the exemplary embodiment, a tolerance equalisation spring 38 is axially tensed between the sliding sleeve 20 and the slaving means 25. In principle, however, the sliding sleeve 20 and the slaving means 25 could also be rigidly connected to each other with respect to the axial direction. In any event, a rotational movement about the longitudinal axis L is possible between the sliding sleeve 20 and the slaving means 25. In this respect, the rotational joint between the dosing and activating means and the rear casing portion 2 is formed between the sliding sleeve 20 and the slaving means 25.

How the gear components 20, 25 and 30 are assembled and arranged relative to the piston rod holder 6 can be perceived in FIG. 8. The mutually facing collars 31, 61 of the reservoir holder 30 and piston rod holder 6 in particular can for instance be recognized, between which the reservoir holding spring 37 is tensed. The reservoir holder 30 comprises a circular cylindrical front sleeve part including a collar 31. Multiple shoes 32 project backwards from the sleeve part. A locking cam 34 which protrudes radially outwards is formed at the rear end of each of the shoes 32. Furthermore, each of the shoes 32 comprises lateral guides 33. The reservoir holder 30 together with its shoes 32 can be inserted between a radially outer and middle sleeve part of the piston rod holder 6. To this end, a sleeve base of the piston rod holder 6 comprises cavities corresponding to the shoes 32. The piston rod holder 6 and the reservoir holder 30 are connected to each other, secured against rotating, via the shoes 32 and the cavities. From the rear side, the slaving means 25 is pushed onto the reservoir holder 30 via the middle sleeve part of the piston rod holder 6. Tongues 27 project from a rear sleeve part of the slaving means 25, corresponding in number and arrangement to the shoes 32. Each one of the tongues 27 is pushed onto one of the shoes 32 and locked by means of the locking cams 34, wherein the locking cams 34 lock into cavities 28 formed correspondingly on the tongues 27. The connection between the slaving means 25 and the reservoir holder 30 can be regarded as substantially completely rigid.

The sliding sleeve 20 comprises a rear sleeve part and a plurality of elastically bending tongues 23, which project from the sleeve part and protrude toward the slaving means 25 in the advancing direction V. Slaving cams 24 are formed at the front ends of the tongues 23 and project radially outward from the tongues 23. When the slaving means 25 moves axially, the sliding sleeve 20 is slaved or driven by an engagement which exists when the slaving cams 24 are connected to a slaving collar 26 which protrudes radially inward at the rear end of the slaving means 25 and which the slaving cams 24 grip behind when connected. The engagement simultaneously enables relative rotational movements about the longitudinal axis L.

Furthermore, it can also be recognized in FIG. 8 how the mechanism holder 5 and the piston rod holder 6 are connected, secured against shifting and secured against rotating. Elastically bending tongues 63, comprising locking cams 64 protruding radially outward, project backwards from the sleeve part of the piston rod holder 6. Via the locking cams 64, the piston rod holder 6 locks in corresponding cavities 52 of the mechanism holder 5. Furthermore, a block against rotating between the mechanism holder 5 and the piston rod holder 6 is obtained by engaging a guiding protrusion 62, which axially projects from the piston rod holder 6, with a guiding cavity 51 of the mechanism holder 5. The mechanism holder 5 and the piston rod holder 6 are connected to each other, secured against shifting and secured against rotating, via the locking connection of the locking cam 64 and the guide of the guiding protrusion 62. The mechanism holder 5 is connected to the rear casing portion 2, secured against shifting and secured against rotating, such that the same also applies to the piston rod holder 6.

A restoring spring 36 is axially tensed between the piston rod holder 6 and the transfer element 10 of the dosing and activating means. The restoring spring 36 serves to restore or reset the dosing and activating means, the split dosing member and the piston rod 4 after the product has been delivered.

In one embodiment, the device in accordance with the present invention further comprises a dosage indicator sleeve 40, which is provided on its outer surface area with a dosage scale 41. The dosage indicator sleeve 40 is shown in a three-dimensional view from the side in each of FIGS. 8 and 9, and in two longitudinal sections, a front view and a rear view in FIG. 10. It is in threaded engagement with the mechanism holder 5. The threaded engagement exists between an outer thread 53 in a rear portion of the mechanism holder 5 and an inner thread 42 of the dosage indicator sleeve 40. The threaded axis of the two threads 42 and 53 coincides with the longitudinal axis L. The dosage scale 41 is formed by dosage values arranged, encircling in a spiral, on the outer surface area of the dosage indicator sleeve 40. In the exemplary embodiment, numbers corresponding to the dosage units which can be selected form the dosage values. The dosage indicator sleeve 40 is connected to the dosing sleeve 7 such that it can be axially and linearly shifted, but is secured against rotating with respect to the longitudinal axis L. For this purpose, the rear end of the dosage indicator sleeve 40 comprises a plurality of radially projecting guiding cams 43 which protrude into and are axially and linearly guided in corresponding guiding grooves 7b (FIG. 9) on the inner surface area of the dosing sleeve 7. Due to this engagement, the dosage indicator sleeve 40 is also rotated about the longitudinal axis L when the dosing sleeve 7 is rotated. Due to the threaded engagement with the mechanism holder 5, the dosage indicator sleeve 40 is thus screwed backwards, counter to the advancing direction V, relative to the mechanism holder 5 and, therefore, also relative to the rear casing portion 2, when the dosage is selected by rotating the dosing sleeve 7.

The portion of the dosage indicator sleeve 40 which forms the inner thread 42 and the dosage scale 41 protrudes or extends into an annular gap which remains between the rear casing portion 2 and the mechanism holder 5. In the radially outer portion opposing the dosage scale 41, the rear casing portion 2 comprises a window 3 through which the dosage scale 41 can be read. The pitch of the inner thread 42 corresponds to the pitch of the spiral dosage scale 41.

The blocking member 45 already mentioned, which due to its form may be referred to in the following as the blocking ring, is arranged radially inwards from a longitudinal portion of the dosage indicator sleeve 40, which protrudes backwards beyond the mechanism holder 5. The blocking ring 45 is mounted, secured against rotating and secured against shifting axially, in a sleeve part of a blocking ring holder 47. The blocking ring holder 47 is fastened, secured against rotating and shifting, to the mechanism holder 5, via a guiding area 54 of the mechanism holder 5 and a locking connection formed between a locking cam 55 of the mechanism holder 5 and a cavity 48 of the blocking ring holder 47 (FIG. 8).

Figure 10:
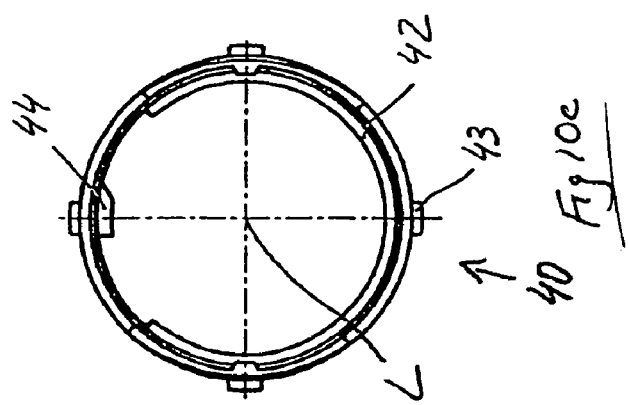
FIG. 10, including
Figure 10:
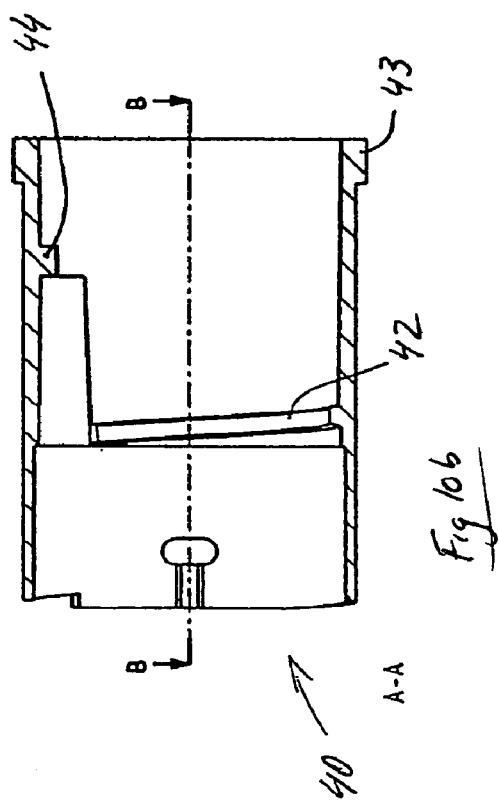
Figure 10:
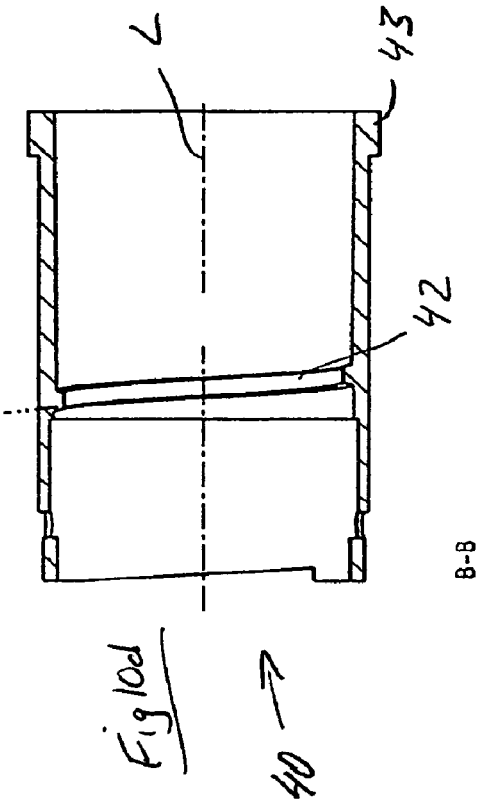
Figure 10:
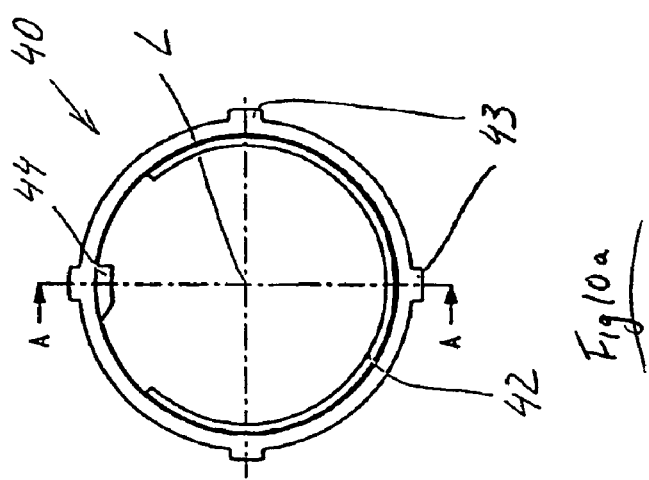

The blocking ring 45 forms a counter reset cam 46 which protrudes radially outwards from the outer surface area of the blocking ring 45 towards the dosage indicator sleeve 40. A reset cam 44 projects radially inwards from the facing inner surface area of the dosage indicator sleeve 40 (FIG. 10). The reset cam 44 is formed in a rotational angular position with respect to the dosage scale 41, such that it is in radial alignment with the counter reset cam 46 and presses radially against the cam 46 precisely when the dosage indicator sleeve 40 assumes a zero-dosage position relative to the rear casing portion 2, in which the dosage value corresponding to the zero-dosage is indicated in the window 3. If the dosage indicator sleeve 40 assumes a position with respect to the mechanism holder 5 and the rear casing portion 2 which does not correspond to the zero-dosage, then the counter reset cam 46 is free from the reset cam 44, i.e., a radially slight distance remains between the counter reset cam 46 and the facing inner surface area of the dosage indicator sleeve 40.

The blocking ring 45 can be moved linearly relative to the blocking ring holder 47, radially with respect to the longitudinal axis L. Diametrically opposite the Counter reset cam 46 with respect to the longitudinal axis L, the spring element 49 is arranged between the blocking ring 45 and the blocking ring holder 47 and presses the blocking ring 45 against the outer surface area of the dosing and activating button 8. The spring element 49 acts as a pressure spring.

The functionality and method of operation of the device in accordance with the present invention is described below with reference to FIGS. 1 to 3, in each of which the device is shown in a different state. Reference should also additionally be made to the other figures.

In FIG. 1, the device assumes an initial state in which the reservoir R is completely filled with the product and from which the dosage can be selected. The dosage indicator sleeve 40 assumes its position corresponding to the zero-dosage, i.e., the dosage value corresponding to the zero-dosage can be read through the window 3. The dosing and activating means (comprising, in one embodiment, the dosing sleeve 7, dosing and activating button 8 and transfer element 10), together with the piston rod 4, assumes its rearmost position, in which the dosage is selected. In this dosage selection position, a slight axial distance $H_1$ remains between the piston rod 4 and the piston K. An equally large, slight axial distance $H_2$ remains between two stopper areas which face each other axially, one of which is formed by the piston rod holder 6 and the other of which is formed by the transfer element 10 and which define a front end position for the transfer element 10 and the piston rod 4. The slight axial distance $H_2$ between this pair of stopper areas is the maximum stroke of the piston rod 4. Selecting the dosage reduces the slight axial distance $H_1$ between the piston K and the piston rod 4. If, within the context of the delivery movement, the piston rod 4 is then moved in the advancing direction V by the always equally long stroke $H_2$ as far as its front end position, then the reduction in the slight distance $H_1$ between the piston rod 4 and the piston K while selecting the dosage corresponds to the product dosage delivered.

The split dosing member (comprising, in one embodiment, dosing members 11, 12) is coupled to the dosage indicator sleeve 40 via the dosing and activating means, such that the axial distance $H_1$ between the piston K and the piston rod 4 is at a maximum, i.e., $H_1=H_2$, when the dosage indicator sleeve 40 assumes its zero-dosage position.

To select the dosage, the dosing sleeve 7 is rotated about the longitudinal axis L relative to the rear casing portion 2, wherein the dosing and activating button 8 is also rotated due to its engagement, secured against rotating, with the dosing sleeve 7. Due to these connections, secured against rotating, the transfer element 10 and therefore also the split dosing member are also necessarily rotated together. Since the piston rod 4 is axially and linearly guided by the piston rod holder 6, the rotational movement of the split dosing member causes a dosing movement of the piston rod 4 directed in the advancing direction, via the threaded engagement. This shortens the slight distance $H_1$ between the piston rod 4 and the piston K by a length corresponding to the selected product dosage; it does not alter the slight distance $H_2$.

Due to its engagement, secured against rotating, the dosage indicator sleeve 40 is slaved or driven correspondingly by the dosing sleeve 7 during the rotational dosing movement and rotated about the longitudinal axis L relative to the mechanism holder 5. Due to the threaded engagement between the mechanism holder 5 and the dosage indicator sleeve 40, an axial movement counter to the advancing direction V is superimposed on the rotational movement of the dosage indicator sleeve 40. As an aside, it may be mentioned that the pitch of the engaged threads 42 and 53 of the dosage indicator sleeve 40 and mechanism holder 5 is greater than the pitch of the engaged threads of the piston rod 4 and split dosing member. Correspondingly, the axial path which the dosage indicator sleeve 40 travels per revolution is larger than the axial path by which the piston rod 4 is moved per revolution of the split dosing member. This benefits the legibility of the dosage scale 41. As soon as the dosage indicator sleeve 40 has been moved, relative to the mechanism holder 5, out of its zero-dosage position by at least one dosage unit, the blocking ring 45 is free from the reset cam 44. The dosage value which can be read on the dosage scale 41 through the window 3 corresponds to the axial length by which the distance $H_1$ is shortened by the dosing movement.

In order to deliver the selected product dosage through the outlet A of the reservoir R, the dosing and activating button 8 is pressed in the advancing direction V, into the rear casing portion 2, i.e., it is activated. The advancing direction V is therefore also simultaneously the activating direction of the dosing and activating button 8. Activating the dosing and activating button 8 also moves the components which are connected, secured against shifting axially, to the dosing and activating button 8, namely the transfer element 10, the split dosing member and, due to the threaded engagement also the piston rod 4, in the advancing direction V by the stroke length $H_2$. During this stroke movement, the piston K is advanced in the advancing direction V by a path length which corresponds to the length by which the slight distance $H_1$ between the piston rod 4 and the piston K is shortened as compared to the stroke $H_2$ by selecting the dosage.

FIG. 2 shows the exemplary device in an end state in which, after repeated administering, the maximum product amount which can be delivered from the reservoir R with the aid of the device has been delivered, i.e., the reservoir R has been emptied. The dosing and activating button 8 has been pressed into the rear casing portion 2 by the stroke length $H_2$. In this axial position of the dosing and activating button 8, its groove 9 is in radial alignment below the blocking ring 45. The groove 9 is slightly wider in the radial direction than the blocking ring 45, in order to still be able to accommodate the blocking ring 45 when the dosing and activating button 8 is spring-deflected. For the pressure from the user, required for activating the dosing and activating button 8, spring-deflects the dosing and activating button 8 a little way into itself, in the front end position of the transfer element 10 and the piston rod 4, which is regarded as touch-sense pleasant. Since the blocking ring 45 is tensed against the outer surface area of the dosing and activating button 8 by the spring element 49, the blocking ring 45 is inserted radially into the groove 9 which is then accessible for it. The larger width of the groove 9 as compared to the blocking ring 45, in combination with the axial spring-deflection of the dosing and activating button 8, increases the reliability that the blocking ring 45 will indeed be inserted into the groove 9 and the dosing and activating means blocked. The blocking ring 45 forms an axial stopper for the spring-deflection movement of the dosing and activating button 8. Diametrically opposite the spring element 49, inserting the blocking ring 45 moves its counter reset cam 46 radially towards the inner surface area of the dosage indicator sleeve 40. Since the blocking ring 45 is connected to the mechanism holder 5 such that it cannot move axially in the blocking ring holder 47, the dosing and activating button 8 and therefore the piston rod 4 together cannot be moved back again counter to the advancing direction V, i.e., the blocking ring 45 and the dosing and activating button 8 are in a blocking engagement. Thus, in the foremost position of the dosing and activating means, the blocking-engaged blocking ring 45 seated in the groove 9 forms an axial block for the dosing and activating means, the split dosing member and the piston rod 4. In this end state, the restoring spring 36 is axially pressure-tensed. The restoring spring 36 is prevented from being relieved by the axial block formed by the blocking ring 45. This axial block ensures that the product can only be selected anew from a defined position of the dosage indicator sleeve 40. This defined position is preferably—as in the exemplary embodiment—the zero-dosage position, i.e., the position in which the zero-dosage can be read on the dosage scale 41 through the window 3.

In order to exchange the emptied reservoir R for a new reservoir R, the two casing portions 1, 2 are screwed apart. Due to the screwing procedure, the casing portions 1, 2 are moved axially relative to each other. During the movement of casing portions 1, 2 which lengthens the casing, the tensed reservoir holding spring 37 presses the reservoir holder 30 relative to the piston rod holder 6 in the advancing direction V until it abuts a stopper formed by the rear casing portion 2. Before the screwing movement is begun, a sufficiently large, slight distance remains axially between a front end of the reservoir holder 30 and the stopper formed by the rear casing portion 2, to enable the reservoir holder 30 to move axially relative to the piston rod holder 6.

As the reservoir holder 30 moves axially relative to the piston rod holder 6, it slaves the slaving means 25 and the sliding sleeve 20. Due to the axial movement of the sliding sleeve 20, the two sliding pieces 15, 16 move radially outwards on the oblique guiding rails 21, 22 of the sliding sleeve 20. As they move radially outwards in this way, the sliding pieces 15, 16 are linearly guided by the mechanism holder 5 and the piston rod holder 6. Since the stays 17 of the sliding piece 15 grip behind the first dosing member 11 and the stays 17 of the sliding piece 16 grip behind the second dosing member 12, the first dosing member 11 and the second dosing member 12 are moved radially apart in the same way, and are thus moved out of their threaded engagement with the piston rod 4. The axial movement which the rear casing portion 2 performs relative to the front casing portion 1 in order to release the engagement between the piston rod 4 and the dosing members 11, 12 may be referred to as a disengaging movement. The disengaging movement moves each of the dosing members 11, 12 to a position retracted from the piston rod 4. In the opposite, engaging movement, in which the rear casing portion 2 performs an axial movement in the reverse direction relative to the front casing portion 1, the dosing members 11, 12 are moved back into engagement with the piston rod 4 by the cam gear formed by sliding sleeve 20 and the sliding pieces 15, 16. Starting with the casing portions 1, 2 completely screwed together, the disengaging movement and the engaging movement occur in a first portion of the screwing movement. This first portion of the screwing movement is complete when the reservoir holding spring 37 has pressed the reservoir holder 30 against the stopper formed by the rear casing portion 2.

FIG. 3 shows the device in a state in which the threaded engagement between the split dosing member and the piston rod 4 has been released and the piston rod 4 can thus be freely shifted axially in the piston rod holder 6. The rear casing portion 2 has just completed its disengaging movement. In the state shown, the piston rod 4 has already been reset to its rearmost position. The piston rod 4 can thus slide back, guided by the piston rod holder 6, to the end position shown, for example by gently tilting the entire device. At the rear end of the dosing button 8, a rubber stopper projects inwards in the advancing direction V and gently damps or stops the sliding movement of the piston rod 4.

As the casing portions 1, 2 are screwed further apart, the positions assumed by the dosing members 11, 12, the sliding pieces 15, 16, the sliding sleeve 20 and the reservoir holder 30 relative to the rear casing portion 2 are no longer altered. This is ensured by the reservoir holder 30 abutting the rear casing portion 2. The two casing portions 1, 2 can be screwed completely apart and the spent reservoir R exchanged for a new one. After a new reservoir R has been inserted into the front casing portion 1, the two casing portions 1, 2 are screwed back together. In the final portion of the screwing movement, the rear casing portion 2 performs its engaging movement relative to the front casing portion 1, in which the reservoir holder 30 comes into contact with the reservoir R or a reservoir holder and is pressed by the latter axially towards the piston rod holder 6, against the spring force of the reservoir holding spring 37. As it axially moves, the reservoir holder 30 also presses the sliding sleeve 20, via the slaving means 25, backwards counter to the advancing direction V. This moves the sliding pieces 15, 16 radially inwards via their guiding engagement with the sliding sleeve 20, until the synchronous engagement between the dosing members 11, 12 and the piston rod 4 is re-established.

Where, in the above, resetting the piston rod 4 is only described for a completely spent reservoir R, it should be noted that the piston rod 4 can also be reset in accordance with the invention from any other axial position of the piston rod 4 in which the piston rod 4 has been moved out of its rearmost position shown in FIG. 1 by a rotational dosing movement by the split dosing member.

When the dosing and activating button 8 is pressed into in the rear casing portion 2 to its foremost position, as in FIGS. 2 and 3, there is no longer a block against rotating between the dosing sleeve 7 and the dosing and activating button 8, i.e., the dosing sleeve 7 can be freely rotated about the longitudinal axis L relative to the dosing and activating button 8 and rear casing portion 2. However, the block against rotating between the dosing sleeve 7 and the dosage indicator sleeve 40 still exists. In order to return the dosing and activating button 8 and, therefore, the dosing and activating means and split dosing member together to the dosage selection position, the dosing sleeve 7 is rotated about the longitudinal axis L in a rotational direction which guides the dosage indicator sleeve 40 back to the zero-dosage position. During this rotational movement, the dosage indicator sleeve 40 is rotated relative to the mechanism holder 5. As a result of the threaded engagement with the mechanism holder 5, the dosage indicator sleeve 40 completes a translational and rotational movement relative to the mechanism holder 5 and rear casing portion 2, towards its zero-dosage position. In a final movement portion before reaching the zero-dosage position, the length of which corresponds to a single settable dosage unit, the reset cam 44 of the dosage indicator sleeve 40 radially overlaps with the counter reset cam 46 of the blocking ring 45. The reset cam 44 is tapered in the circumferential direction on the side which presses against the counter reset cam 46 while the dosage indicator sleeve 40 is rotated back. Tapering enables the two cams 44 and 46 to gradually and gently slide over each other. The reset cam 44, which gradually lengthens radially inwards in its tapered region, moves the blocking ring 45 radially out of the groove 9, against the restoring force of the spring element 49. The axial block is thus released, and the restoring spring 36 presses the dosing and activating means, together with the piston rod 4, back to the initial position shown in FIG. 1.

The sequence of selecting the dosage, delivering the selected dosage by activating the dosing and activating means, axially blocking with the blocking ring 45 via the cam 46, rotating the dosage indicator sleeve 40 back to the zero-dosage position and thus releasing the axial block and springing the dosing and activating means 7/8/10 back to the initial position, can be repeated until the reservoir R has been emptied. The cam 46 and reset cam 44 co-operating couples the movement of the dosing and activating means back to the initial position, from which a dosage can be selected anew, to the zero-dosage position of the dosage indicator sleeve 40.

This coupling is advantageously configured such that the movement of the dosing and activating means is only possible when the dosage indicator sleeve 40 assumes its zero-dosage position, and no other hand operations are required in order to trigger the resetting movement of the dosing and activating means.

In one embodiment of the present invention, the product delivery device of the exemplary embodiment may be used with or provided for an inhaler such as those known to those skilled in art, using which insulin is administered via the airways. The device of the invention serves to dose and deliver the product into an atomising chamber. The product thus provided in doses in the atomising chamber is atomised by an atomising means and administered through a chamber outlet via the airways, preferably orally. The front end of the front casing portion 1 is provided with a connector G formed as a thread, in order to be able to connect the device to the atomising chamber by threaded engagement.

In some embodiments of the present invention, the device can also easily be used directly as an injection apparatus, by screwing a needle holder comprising an integrated injection needle of preferably 30 G or thinner, for example 31 G, onto the front end of the front casing portion 1.

In some embodiments, the device in accordance with the present invention could also be used with or provided for a pressure injector and, in this instance, be connected to a discharge means of the pressure injector. The device would supply the selected product dosage to the discharge means and the discharge means would discharge said product dosage at high pressure through an injection nozzle.

In the foregoing description, embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An administering apparatus for administering an injectable product in doses, said administering apparatus comprising:
   a) a casing with a reservoir for the product;
   b) a conveying means which acts on the product in order to deliver a selected product dosage from the reservoir;
   c) a dosing and activating means which performs a dosing movement for selecting the product dosage in a dosage selection position and performs a delivery movement in an activating direction as far as a front end position, for delivering the selected product dosage, and which is coupled to the conveying means such that the delivery movement causes the selected product dosage to be delivered;
   d) a dosage indicator sleeve which is coupled to the dosing and activating means such that the dosage indicator sleeve is moved relative to the casing by the dosing movement of the dosing and activating means, in order to indicate the selected product dosage; and
   e) a blocking member which is in a blocking engagement with the dosing and activating means in the front end position of the dosing and activating means to prevent the dosing and activating means from moving counter to the activating direction;
   f) wherein the blocking member can be moved out of the blocking engagement against an elasticity force;
   g) wherein a reset cam protrudes from the dosage indicator sleeve, via which the dosage indicator sleeve presses the blocking member out of the blocking engagement, when the dosage indicator sleeve is moved to a zero-dosage position relative to the casing; and
   h) wherein a counter reset cam protrudes from the blocking member, and wherein the reset cam presses against the counter reset cam in the zero-dosage position of the dosage indicator sleeve.

2. The administering apparatus as set forth in claim 1, wherein the dosage indicator sleeve surrounds the blocking member and the reset cam protrudes from an inner surface area of the dosage indicator sleeve.

3. The administering apparatus as set forth in claim 2, wherein the reset cam is widened on at least one side, as far as the inner surface area of the dosage indicator sleeve.

4. The administering apparatus as set forth in claim 1, wherein the blocking member is formed by an at least partially annular body, and the elasticity force acts on a side of the at least partially annular body opposite the counter reset cam with respect to a central longitudinal axis of the at least partially annular body and is directed towards the counter reset cam.

5. The administering apparatus as set forth in claim 1, wherein the dosage indicator sleeve is connected to the casing via a threaded engagement which defines the movement of the dosage indicator sleeve.

6. The administering apparatus as set forth in claim 5, further comprising a mechanism holder connected to the casing such that it cannot move with respect to the dosing movement and the delivery movement, said mechanism holder comprising an outer thread and the dosage indicator sleeve comprising an inner thread, said threads in engagement with each other.

7. The administering apparatus as set forth in claim 1, wherein an upper surface area of the dosage indicator sleeve comprises a dosage scale which encircles a longitudinal axis of the dosage indicator sleeve in a spiral.

8. The administering apparatus as set forth in claim 1, wherein the blocking member is permanently pressed against the dosing and activating means, transversely with respect to the activating direction, by the elasticity force, and the dosing and activating means comprises a cavity in a portion against which the blocking member presses during the delivery movement of the dosing and activating means, wherein the blocking member is pressed into said cavity in order to establish the blocking engagement in the front end position of the dosing and activating means.

9. The administering apparatus as set forth in claim 1, wherein the dosing and activating means comprises an activating part which protrudes backwards out of the casing and can be moved in the activating direction relative to a transfer means of the dosing and activating means, against an elasticity force, in order to enable the dosing and activating means to spring-deflect in the front end position.

10. The administering apparatus as set forth in claim 9, wherein the blocking member forms the blocking engagement with the activating part.

11. The administering apparatus as set forth in claim 10, wherein the blocking member forms a stopper for the activating part, wherein said stopper stops the activating part moving in the activating direction.

12. The administering apparatus as set forth in claim 1, wherein the dosing and activating means is connected to the dosage indicator sleeve, secured against rotating in the dosage selection position but such that it can move in the activating direction relative to the dosage indicator sleeve.

13. The administering apparatus as set forth in claim 1, wherein the operable coupling between the dosing and activating means and the dosage indicator sleeve causes the dosage indicator sleeve to be slaved during the dosing movement of the dosing and activating means, but permits the delivery movement of the dosing and activating means relative to the dosage indicator sleeve.

14. The administering apparatus as set forth in claim 13, wherein the operable coupling is released in the front end position of the dosing and activating means.

15. The administering apparatus as set forth in claim 1, wherein the dosing movement is a rotational movement about a rotational axis and the delivery movement is a translational movement along the rotational axis.

* * * * *